(12) United States Patent
Bedre et al.

(10) Patent No.: US 12,644,885 B2
(45) Date of Patent: Jun. 2, 2026

(54) FLUORESCENT MICROSPHERES EVENLY COATED WITH MAGNETIC PARTICLES AND METHODS OF USE

(71) Applicant: Emission Inc., Georgetown, TX (US)

(72) Inventors: Jason A. Bedre, Georgetown, TX (US); Don Joseph Chandler, Austin, TX (US); Gilberto M. Villacorta, Arlington, VA (US)

(73) Assignee: Emission Inc., Georgetown, TX (US)

( * ) Notice: Subject to any disclaimer, the term of this patent is extended or adjusted under 35 U.S.C. 154(b) by 530 days.

(21) Appl. No.: 18/202,581

(22) Filed: May 26, 2023

(65) Prior Publication Data

US 2023/0384299 A1     Nov. 30, 2023

Related U.S. Application Data

(63) Continuation of application No. PCT/US2021/048560, filed on Aug. 31, 2021.

(Continued)

(51) Int. Cl.
| | |
|---|---|
| *G01N 33/543* | (2006.01) |
| *B01J 13/22* | (2006.01) |
| *C09B 67/02* | (2006.01) |

(52) U.S. Cl.
CPC ........ *G01N 33/54326* (2013.01); *B01J 13/22* (2013.01); *C09B 67/0097* (2013.01)

(58) Field of Classification Search
CPC .. G01N 21/64; G01N 33/54326; B82Y 25/00; Y10T 428/2991; Y10T 428/2996; Y10T 428/32
See application file for complete search history.

(56) References Cited

U.S. PATENT DOCUMENTS

| | | | |
|---|---|---|---|
| 3,948,846 | A | 4/1976 | Waters |
| 4,677,045 | A | 6/1987 | Champ et al. |

(Continued)

FOREIGN PATENT DOCUMENTS

| | | | |
|---|---|---|---|
| JP | 2005-048104 A | 2/2005 | |
| WO | WO-2004001414 A1 * | 12/2003 | ....... G01N 33/54346 |

(Continued)

OTHER PUBLICATIONS

Invitation to Pay Additional Fees for International Application No. PCT/US2021/048560 dated Dec. 13, 2021.

(Continued)

*Primary Examiner* — Hoa (Holly) Le
(74) *Attorney, Agent, or Firm* — Wolf, Greenfield & Sacks, P.C.

(57) ABSTRACT

Magnetic or non-magnetic microspheres, populations of magnetic or non-magnetic microspheres, and methods for forming magnetic or non-magnetic microspheres are provided. One microsphere configured to exhibit fluorescent and magnetic properties includes a core particle and a monolayer of magnetic particles coupled to a substantial portion of a surface of a core particle. About 60% to about 90% of a surface of a core particle is covered by the monolayer of magnetic particles. The microsphere also includes an outer polymer layer surrounding or encapsulating both the monolayer of magnetic particles and the core particle. One population of magnetic or non-magnetic microspheres is configured to exhibit fluorescent and magnetic properties includes two or more subsets of magnetic fluorescent microspheres. The two or more subsets of microspheres are configured to exhibit different fluorescent and/or magnetic properties. Individual microspheres in the two or more subsets are configured as described herein.

20 Claims, 10 Drawing Sheets

Related U.S. Application Data

(60) Provisional application No. 63/182,505, filed on Apr. 30, 2021, provisional application No. 63/119,447, filed on Nov. 30, 2020.

(56) References Cited

U.S. PATENT DOCUMENTS

| | | | |
|---|---|---|---|
| 5,237,498 | A | 8/1993 | Tenma et al. |
| 5,354,873 | A | 10/1994 | Allen et al. |
| 5,492,795 | A | 2/1996 | Allen et al. |
| 5,656,750 | A | 8/1997 | Allen et al. |
| 5,795,981 | A | 8/1998 | Lee et al. |
| 6,010,812 | A | 1/2000 | Barbetta et al. |
| 6,013,531 | A | 1/2000 | Wang et al. |
| 6,599,331 | B2 | 7/2003 | Chandler et al. |
| 7,214,640 | B2 | 5/2007 | Margetts |
| 7,378,035 | B2 | 5/2008 | Margetts |
| 2004/0139565 | A1 | 7/2004 | Banerjee et al. |
| 2010/0233734 | A1 | 9/2010 | Hobbs |
| 2014/0042366 | A1* | 2/2014 | Chandler ............... H01F 1/111 |
| | | | 427/131 |
| 2017/0080112 | A1 | 3/2017 | Ishow et al. |
| 2020/0071439 | A1 | 3/2020 | Bardman et al. |
| 2023/0352218 | A1* | 11/2023 | Luo .................. G01N 33/54326 |

FOREIGN PATENT DOCUMENTS

| | | | |
|---|---|---|---|
| WO | WO 2021/114040 | A1 | 6/2021 |
| WO | WO 2021/114042 | A1 | 6/2021 |
| WO | WO 2021/114057 | A1 | 6/2021 |
| WO | WO 2021/114058 | A1 | 6/2021 |

OTHER PUBLICATIONS

International Preliminary Report on Patentability (Chapter 1) for International Application No. PCT/US2021/048560 dated Jun. 15, 2023.

[No Author Listed], Superparamagnetic Particles. Agilent LodeStars. Agilent Technologies. Aug. 23, 2016: 8 pages.

Cantarero et al., The adsorptive characteristics of proteins for polystyrene and their significance in solid-phase imunoassays. Anal Biochem. Jul. 1, 1980;105(2):375-82. doi: 10.1016/0003-2697(80)90473-x.

Colvin et al., The Covalent Binding of Enzymes and Immunoglobulins to Hydrophilic Microspheres. In: Microspheres: Medical and Biological Applications. Nov. 2017. Rembaum et al., Eds. Chapter 1:1-13.

Illum et al., Attachment of monoclonal antibodies to microspheres. Methods Enzymol. 1985;112:67-84. doi: 10.1016/s0076-6879(85)12008-2.

Law et al., Squaraine chemistry. Synthesis, characterization, and optical properties of a class of novel unsymmetrical squaraines: [4-(dimethylamino)phenyl](4'-methoxyphenyl)squaraine and its derivatives. J Org Chem. Jun. 1, 1992;57(12):3278-86. doi: 10.1021/jo00038a010.

Maahs et al., Syntheses and Derivatives of Squaric Acid. Angew Chem. Oct. 1966;5(10):888-93. doi: 10.1002/anie.196608881.

Philippova et al., Magnetic polymer beads: Recent trends and developments in synthetic design and applications. Eur Polym J. Apr. 2011;47(4):542-99. doi: 10.1016/j.eurpolymj.2010.11.006.

Sprenger et al., Cyclobutendiylium-Farbstoffe. Angew Chem. Jul. 21, 1968;80(14):541-6. doi: 10.1002/ange.19680801402.

Sprenger et al., Das Cyclobuten-diylium-Kation, ein neuartiger Chromophor aus Quadratsäure. Angew Chem. Jun. 21, 1967;79(12):581-2. doi: 10.1002/ange.19670791217.

International Search Report and Written Opinion issued in International Patent Application No. PCT/US2021/048560, dated Mar. 4, 2022.

* cited by examiner $y = -8.3176x + 3017$ $y = -3.7539x + 3265.8$

FLUORESCENT MICROSPHERES EVENLY COATED WITH MAGNETIC PARTICLES AND METHODS OF USE

This application is a continuation of International Patent Application Serial No. PCT/US2021/048560, filed Aug. 31, 2021, which claims the benefit of and priority to U.S. Provisional Patent Application No. 63/182,505, filed Apr. 30, 2021, and U.S. Provisional Patent Application No. 63/119,447, filed Nov. 30, 2020, the entire disclosures of each of which are incorporated by reference herein.

RELATED APPLICATIONS

The present disclosure generally relates to a next generation magnetic microspheres for use in next generation fluorescence-based applications. Certain embodiments relate to a microsphere that includes a monolayer of magnetic particles coupled to and evenly coating a substantial portion of a surface of a core particle. The core particle comprised of a first cross-linked or non-cross-linked polymer composition and exhibiting tunable density (or buoyancy) characteristics. The monolayer of magnetic particles and the core microsphere are surrounded by an outer layer of a second cross-linked or non-cross-linked polymer composition.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Figure 1:
FIG. 1 is an optical image of an Eppendorf tube containing next generation microspheres suspended/dispersed in an aqueous solution in an absence of an external magnetic field.

For many purposes, appropriate microspheres display paramagnetism or superparamagnetism, rather than ferromagnetism. Such, microspheres have negligible magnetism in the absence of a magnetic field, but application of a magnetic field induces alignment of the magnetic domains in the microspheres, resulting in attraction of the microspheres to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field. This retention of domain alignment may lead to microsphere aggregation in the absence of an external magnetic field, which is often undesirable. Ferromagnetic materials have permanently aligned domains, so microspheres including such magnetic materials will readily aggregate. In a preferred embodiment the magnetic material or particle is $Fe_3O_4$ (magnetite), but any paramagnetic or superparamagnetic material may similarly be used. Examples include, but are not limited to, $Fe_2O_3$, $MnFe_2O_4$, $CoFe_2O_4$, $ZnFe_2O_4$ and $NiFe_2O_4$.

A significant and growing use of magnetic microspheres is in the field of molecular diagnostic assays. Assays for proteins and oligonucleotides can be performed on the surface of the microspheres, which can then be magnetically separated from the reaction mixture before the characteristics of the microspheres are measured. Isolation of the assay microspheres prior to measurement decreases interference of non-target molecules with the measurements thereby producing more accurate results.

The core particle is produced through the copolymerization of a variety of vinyl monomers. In a preferred embodiment these are styrene, t-butylstyrene, acrylic acid and divinylbenzene. Those skilled in the art will recognize that there are numerous other unsaturated monomers that can be readily added or substituted in place of the preferred unsaturated monomers. Divinylbenzene functions as a crosslinker, but many dienes will also serve this purpose, such as ethylene glycol dimethacrylate, butadiene, trimethylol propane trimethacrylate, N,N'-methylene-bis-acrylamide and the like, or this crosslinker can be omitted if the particle will not be exposed to solvents that may dissolve a core particle comprised of a non-cross-linked polymer composition. Similarly, the acrylic acid functions to help dispersibility in aqueous or polar environments, as well as provide functional groups on the surface of the core particle to assist in immobilizing the magnetic material or particle. It will be apparent to the experienced practitioner that several polymerizable (unsaturated) functionalized monomers can be readily added or substituted in place of the preferred unsaturated functionalized monomers to provide the same general characteristics. Functionalized olefins, which prove useful in this respect, may have carboxyl, amino, sulfhydryl, epoxy, hydroxy, halide and other heteroatom containing functional groups. Other unsaturated functionalized monomers that might be desirable include, but are not limited to, those providing functional groups such as carboxylates, esters, alcohols, carbamides, aldehydes, amines, sulfur oxides, nitrogen oxides, or halides, which may groups facilitate attachment of analytical reactants and/or particle-to-particle bonding. Alternatively, these functional groups can be generated on the surface of the next generation microspheres by further chemical reaction of a polymer having other precursor reactive groups, which can be converted to desired functional group (for example, carboxyl groups can be generated by hydrolysis of anhydrides, such as maleic anhydride, or by oxidation of surface methylol or aldehyde end groups). Other compounds, such as diamines, di hydrazides, mercaptoalkylamines and dimercaptans can be used as linking moieties for later attachment of drugs, enzymes or other reactive species, including nanospheres or nanoparticles.

A key feature of the next generation core particles described here is the tunability of density (or sometimes referred to herein as tunability of buoyancy) that can be achieved through the polymerization of a mixture of unsaturated monomers, including t-butylstyrene. While a polymer of pure polystyrene will have a density of roughly 1.05 g/cm$^3$, and a polymer of pure poly(4-t-butylstyrene) will have a density of approximately 0.95 g/cm$^3$, a polymer comprised of a mixtures of the two or more unsaturated monomers will result in a polymer having a density somewhere in between these two values, Thus, for example, a polymeric core particle arising from a polymerization of a mixture of equal parts styrene and t-butylstyrene, in the presence of small amounts of divinylbenzene and acrylic acid, would exhibit a density of approximately 1.0 g/cm$^3$. Overall, the next generation magnetic microspheres described herein will have a density ranging from about 0.85 g/cm$^3$ to about 1.05 g/cm$^3$, preferably, from about g/cm$^3$ to about 1.00 g/cm$^3$, or preferably from about 0.85 g/cm$^3$ to about 1.02 g/cm$^3$, or preferably from about 005 g/cm$^3$ to about 1.05 g/cm$^3$, One of ordinary skill in the art will appreciate, then, that a "low density" (or LD) microsphere has a density that is less than that of "standard density" (or SD) microsphere comprised of a core particle made from a polymer of 100% polystyrene, A preferred lower bound of density of an LD microsphere (bare, non-magnetic) will be that of a microsphere comprised of a core particle made from a polymer of 100% poly(4-t-butylstyrene).

One of ordinary skill in the art will recognize other suitable cross-linked or non-cross-linked polymer compositions. These compositions include, but are not limited to, brominated polystyrene, polyacrylic acid, polyacrylonitrile, polyimide, polyacrylamide, polyacrolein, polybutadiene, polycaprolactone, polycarbonate, polyester, polyethylene, polyethylene terephthalate, polydimethyl siloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, or combinations thereof. Other suitable polymer compositions can include carbohydrates, e.g., carboxymethyl cellulose, hydroxyethyl cellulose, agar, gel, proteinaceous polymer, polypeptide, poly saturated or unsaturated lipids, resin, latex, rubber, silicone (e.g., polydimethyldiphenyl siloxane), glass, ceramic, charcoal, kaolinite, bentonite and the like.

In a preferred embodiment, an outer polymer shell surrounds or encapsulates the core particle and the monolayer of magnetic particle that evenly coats the surface of the core particle. This outer layer preferably comprises a second cross-linked or non-cross-linked polymer composition arising from a polymerization of a mixture of unsaturated monomers. More preferably, this mixture comprises styrene, divinylbenzene and acrylic acid, but, as is the case with a core particle, these components can be deleted, added, or substituted with other substances to impart a desired characteristic or set of characteristics. Similarly, other suitable monomers may be incorporated to produce desired characteristics and functional groups.

In a preferred embodiment, benzoyl peroxide is used to initiate polymerization, but the skilled artisan will be aware that numerous radical, redox, and photo initiators are well suited for use in such polymerization.

In some embodiments, dyes may or may not be incorporated in the microsphere. Moreover, the dyes may or may not be fluorescent, Choice of dyes would be dependent on the intended use and would be familiar to one of ordinary skill in the art. Dyes may also come in the form of pigments or fluorescent nanoparticles.

Suitable solvents will be selected based on their ability to solubilize the particular class of hydrophobic dyes of interest. It is preferable that their solubility characteristics are substantially similar. The solvents can be acyl, aliphatic, cycloaliphatic, aromatic or heterocyclic hydrocarbons; the solvents may or may not have halogens, oxygen, sulfur, nitrogen, and/or phosphorous as either terminal groups or as integral parts of a ring or chain. Specifically, solvents such as toluene, xylene, hexane, pentane, acetone, DMSO, or methylene chloride can be used. In a preferred embodiment, chlorinated solvents, more preferably chloroform, are used to solubilize the squaric acid class of dyes, which are preferred dyes used in this technology.

In one embodiment two fluorescent squaraine dyes are used, e.g., red dye which is 1,3-bis[(1,3-dihydro-1,3,3-rimethyl-2H-indol-2-ylidene)methyl]-2,4-dihydroxy-cyclobutenediylium, bis(inner salt) and orange dye is 2-(3,5-dimethylpyrrol-2-yl)-4-(3,5-dimethyl-2H-pyrrol-2-ylidene)-3-hydroxy-2-cyclobuten-1-one. The molar ratio between first and second dye, when present in a bead, will preferably be between about 0 and 10,000, more preferably between 0.00001 and 2,000. Both dyes would preferably be excited at the same absorption wavelength, e.g., ranging from ultraviolet to about 800 nm, and emit fluorescent light at two distinct, essentially non-overlapping wavelengths distant from each other by at least 10 nm, preferably 30 nm, and more preferably by at least 50 nm. For example, the emission peak of the dye #1 is at 585 nm, and the peak emission of dye #2 is at 630 nm.

The squaric acid based fluorescent dyes can be synthesized by methods described in the literature, See, for example, Sprenger et al. Angew. Chem., 79, 581 (1967); Angew. Chem., 80, 541 (1968); and Maaks et al., Angew Chem. Intern, Edit., 5, 888 (1966). Briefly, one equivalent of squaric acid (1,2-dihydroxycyclobutenedione) is condensed with two equivalents of an active compound, such as a pyrrole, indoline, or aniline, and refluxed in a mixture of an alcohol and an aromatic solvent (such as benzene) under conditions that allow removal of water from the reaction mixture. The resulting dye can be collected and purified by a number of standard methods, such as recrystallization, distillation, chromatography, etc. Additionally, unsymmetrically substituted squaric acid compounds can be synthesized by methods such as those described by Law et al., J. Org. Chem, 57, 3278, (1992). Specific methods of making some of such dyes are well known in the art and can be found for example in U.S. Pat. Nos. 5,656,750; 5,492,795; 4,677,045; 5,237,498; and 5,354,873, Optionally such dyes will contain functional groups capable of forming a stable fluorescent product with functional groups typically found in biomolecules or polymers including activated esters, isothiocyanates, amines, hydrazines, halides, acids, azides, maleimides, alcohols, acrylamides, haloacetamides, phenols, thiols, acids, aldehydes and ketones.

In addition to specific squaric acid dyes are used in this preferred embodiment, related dyes can be further selected from cyclobutenedione derivatives, substituted cephalosporin compounds, fluorinated squaraine compositions, symmetrical and unsymmetrical squaraines, alkylalkoxy squaraines, or squarylium compounds, Some of these dyes can fluoresce at near infrared as well as at infrared wavelengths that would effectively expand the range of emission spectra up to about 1,000 nm.

In addition to squaraines, i.e., derived from squaric acid, hydrophobic dyes such as phthalocyanines and naphthalocyanines can be also selected as operating at longer wavelengths. Other classes of fluorochromes are equally suitable for use as dyes according to the present technology. Some of these dyes are listed herein: 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy Fl, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Dimino Naphtyl Sulphonic Acid), Dansyl NH—CH3, DAPI, Diamino Phenyl Oxydiazole (DAO), Dimethylamino-5-Sulphonic acid, Dipyrrometheneeboron Difluoride, Diphenyl Brilliant Flavine 7GFF, Dopamine, Eosin, Erythrosin ITC, Ethidium. Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 100GF, Genacryl Pink 3G, Genacryl Yellow SGF, Gloxalic Acid, Granular Blue, Haematoporphyrin, Hoechst 33258 (bound to DNA), Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Ivlaxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin ESG, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron. Yellow L, SITS (Primuline), SITS (Stilbene lsothiosulphonic acid), Stilbene, Snarf I, sulphO Rhodamine B Can C, Suipho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof.

Pacific Blue dye (Invitrogen Molecular Probes, ThermoFisher) is a bright blue-fluorescent dye optimally excited by the 405 nm line of the violet laser and with excitation/emission at 410/455 nm. Pacific Blue, Pacific Green and Pacific Orange dye conjugates can be simultaneously excited at 405 nm and emit at 455 nm, 500 nm and 551 nm, respectively, facilitating three-color dyeing and the preparation of hundreds (up to 1400) bead sets.

One skilled in the art would certainly know which one to select among such dyes as long as desired emission and absorption properties as well as their hydrophobic properties are appropriate. Many absorption/emission profiles are available depending on the chosen dye, including (in nm) 397/440 (blue/violet), 552/570 (green), 635/650 and/or 670/700 (orange/red). The spectral properties of the fluorescent dyes should be sufficiently similar in excitation wavelengths and intensity to fluorescein or rhodamine derivatives as to permit the use of the same flow cytometry equipment. It is preferable that the dyes, however, have higher solubility in organic solvents and have improved photostability and quantum yields. These dyes will be combined at predetermined ratio and embedded into a microsphere vehicle and total dye quantity will be between about 0.00001% and 15% by weight to particle weight. This limitation is however of little consequence to the present technology for as long as the particle impregnated with the dyes is stable and usable for its intended purpose.

Any suitable fluorescent dye can also be used as a reporter. Such reporter dyes can be fluorescein isothiocyanate, fluorescein-5-isothiocyanate, malachite green isothiocyanate, tetramethylrhodamine-5-isothiocyanate, tetramethylrhodamine-6-isothiocyanate, rhodamine b isothiocyanate, R-phycoerythrin and the like.

It will also be apparent to those skilled in the art that discrimination between bead sets can be accomplished by providing microspheres beads of different sizes (diameters). Thus, if microspheres are produced using the methods described herein, and one bead set has a diameter of 4 microns, and a second bead set has a diameter of 6 microns, the two microsphere types can be distinguished by established methodologies, such as characteristic light scatter profiles. It will be further apparent that this size parameter can be used in conjunction with the herein described unique fluorescent signature discrimination to provide an even greater number of distinguishable bead sets.

Additional Embodiments

The following description of various embodiments of microspheres, populations of microspheres, and methods for forming microspheres is not to be construed in any way as limiting the subject matter of the appended claims.

An embodiment relates to a microsphere configured to exhibit fluorescent and magnetic properties. The magnetic microsphere includes a core particle comprising a first polymer composition and a monolayer of magnetic particle coupled to a surface of the core particle. About 60% to about 90% of a surface of the core particle is covered by the monolayer of magnetic particles. In addition, the microsphere includes a second polymer composition surrounding or encapsulating both the monolayer of magnetic particles and the core particle.

In one embodiment, the core particle includes one or more functional groups coupled to the surface of the core particle. In another embodiment, the microsphere includes one or more fluorochromes. In a different embodiment, the microsphere includes two or more different fluorochromes. In some embodiments, the fluorochrome(s) included in the microsphere are incorporated into the outer polymer layer as well as the polymer composition comprising the core particle.

In some embodiments, a substantial portion of the magnetic particles includes particles having a size of about 10 nm to about 100 nm. In a preferred embodiment, a substantial portion of the magnetic particles includes particles having a size of about 5 nm to about 50 nm. In some embodiments, the magnetic particles include single crystals of magnetic material, such as magnetite. In a further embodiment, the magnetic particle includes aggregates of magnetic particles. For instance, the magnetic particle may be aggregates of particles smaller than those described above such that the aggregates have a size in one of the above ranges. In another embodiment, the magnetic particle includes a mixed metal magnetic material. In an additional embodiment, the microsphere includes one or more functional groups coupled to a surface of the core particle or coupled to a surface of an outer polymer layer surrounding or encapsulating both the monolayer of magnetic particles and the core particle.

In one embodiment, the microsphere includes an additional monolayer of magnetic particles coupled to a surface of an outer polymer layer and an additional polymer composition surrounding or encapsulating the additional monolayer of magnetic particles. It will be easily recognized that alternating layers of magnetic particles and polymer may be repeated in the microsphere until the desired magnetic content for the microsphere is achieved. In this manner, the microsphere may include one or more monolayers of magnetic particles/polymer layers, each of which is configured such that about 60% to about 90% of a surface of the core particle is covered with a monolayer of magnetic particles.

In one such embodiment, the magnetic particle and the additional magnetic particle have substantially the same composition. In a different embodiment, the magnetic particle and the additional magnetic particle have different compositions. In a further embodiment, at least one of the magnetic particle and the additional magnetic particle includes a mixed metal magnetic particle. In another such embodiment, the polymer layer and the additional polymer layer are formed of substantially the same polymerizable (unsaturated) material. In other embodiments, the polymer layer and the additional polymer layer are formed of different polymerizable (unsaturated) materials. In some embodiments, the microsphere includes one or more functional groups coupled to an outer surface of the additional polymer layer. Each of the embodiments of the microsphere described above may be further configured as described herein and formed according to method embodiments described herein.

The microsphere embodiments described above provide several advantages over currently used microspheres having magnetic and fluorescent properties. For example, the microsphere described above can include greater than about 2% to about 10% by weight of magnetic particles without significantly hindering light transmission into and out of the microsphere. In addition, the magnetic particle can be strongly associated with the microsphere as described further herein such that the magnetic particle is not released from the microsphere during dyeing. The magnetized core particle is also coated with a polymer layer, which substantially prevents interaction between the magnetic particle and certain biomolecules of interest. Furthermore, the outer polymer layer may be formed in the absence of surfactants and stabilizers.

Another embodiment relates to a population of microspheres configured to exhibit fluorescent and magnetic properties. The population includes two or more subsets of microspheres configured to exhibit different fluorescent properties (i.e., unique fluorescent signatures), different magnetic properties, or different fluorescent and magnetic properties. Individual microspheres in the two or more subsets include a core particle and a monolayer of magnetic particles coupled to a surface of the core particle. About 60% to about 90% of a surface of the core particle is covered by the monolayer of magnetic particle. The individual microspheres also include an outer polymer layer surrounding or encapsulating both the magnetic particle and the core particle. The individual microspheres and the population described above may be further configured as described herein.

An additional embodiment relates to a method for forming microspheres that exhibit magnetic properties. The method includes combining core particle with a monolayer of magnetic particles such that the monolayer of magnetic particles couples to a surface of the core particle to form magnetized core microspheres. About 60%© to about 90% of a surface of a core particle is covered by the magnetic particles, Stated another way, at least about 60%, at least about 70%, at least about 80%© and at least about 90% of a surface of a core particle is covered or evenly coated by a monolayer of magnetic particles. The method also includes combining the magnetized core particles with one or more polymerizable (unsaturated) materials such that the one or more polymerizable (unsaturated) materials form an outer polymer layer surrounding the magnetized core microspheres thereby forming the microspheres that exhibit magnetic properties (i.e., they are sensitive to external magnetic fields).

An important feature of this technology is the use of a core particle of tunable density. By adjusting the ratio of the major styrenic components, the density can be adjusted over a broad range. It is thus possible to construct a magnetically responsive particle with a density tailored to achieve a desired characteristic, such as the rate of settling in a liquid suspension. For example, using a core particle in which the styrenic component is 100% 4-t-butylstyrene, for which the density is approximately 0.95 $g/cm^3$, coated with approximately 5% by weight magnetite, and a thin outer polymer shell, the resulting magnetically responsive particle would have a density of about 1.0 $g/cm^3$. In water this particle would remain suspended indefinitely in the absence of a magnetic field but would easily be isolated through the application of a magnetic field.

When conducting biological assays in conventional buffers, which often have a density greater than 1.0 $g/cm^3$, it is apparent that particles with a density of 1.0 $g/cm^3$, as described above, would likely float on the surface of a suspension solution. While this situation may be desirable in certain cases, such as the separation of the particles from other, denser, suspension components, it is anticipated that many applications will require particles of the same or greater density than a suspending solution, A denser particle will allow a separation of the particles by either magnetic or gravitational (including centrifugation) forces, Thus, it is another aspect of this technology to provide mixtures of styrenic monomers to achieve a desired density. For example, an equimolar mixture of styrene and 4-t-butyl styrene will, when polymerized, result in a particle with a density of approximately 1.0 g/cm$^3$. When coated with 5% by weight of magnetite and a thin outer polymer shell, the resulting particle will have a density of about 1.05 g/cm$^3$. If the same particle is coated with 2% by weight of magnetite and a thin polymer shell, the density would be about 1.02 g/cm$^3$. Similarly, it is possible to construct a particle with a density of 1.02 g/cm$^3$ by starting with a core particle that is 80% t-butyl styrene and 20% styrene, giving a density of about 0.97 g/cm$^3$, then coating with 5% by weight of magnetite followed by a thin outer polymer shell. It is thus apparent that a wide range of particle densities can be achieved through a combination of the ratios of styrenic components and magnetite content. It will also be apparent to those skilled in the art that other monomers, styrenic or non-styrenic can be added or included to expand the possible range of core particle densities.

In some embodiments, the method includes swelling the formed magnetic microspheres in a fluorochrome containing solvent such that the fluorochrome migrates into the formed magnetic microspheres. Such a method also includes changing one or more properties of the fluorochrome containing solvent such that the formed microspheres shrink thereby entrapping the fluorochrome in the formed magnetic microspheres. In another embodiment, the method includes coupling one or more functional groups presented on a surface of an outer polymer layer to a certain reagent to produce, for example, a molecular diagnostic assay, a participant in a chemical reaction, or a catalyst in a chemical, biological, or biochemical transformation. Each of the embodiments of the method described above may include any other step(s) described herein.

This disclosure describes a microsphere comprising (i) a core particle comprised of first cross-linked or non-cross-linked polymer composition arising from a polymerization of a mixture of unsaturated monomers, including t-butyl-styrene, the core particle having an outer surface, (ii) a monolayer of magnetic particles evenly coating a substantial portion of the outer surface of the core particle and (iii) an outer layer of a second cross-linked or non-cross-linked polymer composition arising from a polymerization of a mixture of unsaturated monomers. This microsphere can be dyed by contacting the microsphere with a mixture comprising one or more fluorescent or non-fluorescent dyes. The microspheres can then be treated to apply a monolayer of magnetic particles, which evenly coats at least 60%© of the outer surface of the core particle. In other embodiments, a monolayer of magnetic particles evenly coats at least 70% of the outer surface of the core particle. In another embodiment, a monolayer of magnetic particles evenly coats at least 80% of the outer surface of the core particle. In still other embodiments, a monolayer of magnetic particles evenly coats at least 90% of the outer surface of the core particle. Preferably, a monolayer of magnetic particles evenly coats between 60% and 90% of the outer surface of a core particle.

Thus is provided a microsphere comprising (i) a core particle comprised of first cross-linked or non-cross-linked polymer composition arising from a polymerization of a mixture of unsaturated monomers, including t-butylstyrene, the core particle having an outer surface, (ii) a monolayer of magnetic particles evenly coating a substantial portion of the outer surface of the core particle and (hi) an outer layer of a second cross-linked or non-cross-linked polymer composition arising from a polymerization of a mixture of unsaturated monomers, and which microsphere has been dyed by contacting the microsphere with a mixture comprising one or more fluorescent or non-fluorescent dyes. In one embodiment, a polymerization giving rise to the second cross-linked polymer composition is carried out in the presence of an anhydride. In another embodiment, a polymerization giving rise to the second cross-linked polymer composition is carried out in the presence of free radical initiator. Preferably, a microsphere of the present disclosure possesses a unique fluorescent or non-fluorescent signature. Moreover, the unique fluorescent or non-fluorescent signature arises from exposure to a unique mixture comprising one or more fluorescent or non-fluorescent dyes, or is obtained by varying a concentration of at least one of a mixture comprising one or more fluorescent or non-fluorescent dyes.

The instant disclosure describes a population having two or more sets of microspheres, either segregated by set or combined, each microsphere of each set comprising (i) a core particle comprised of first cross-linked or non-cross-linked polymer composition arising from a polymerization of a mixture of unsaturated monomers, including t-butyl-styrene, the core particle having an outer surface, (ii) a monolayer of magnetic particles evenly coating a substantial portion of the outer surface of the core particle and (iii) an outer layer of a second cross-linked or non-cross-linked polymer composition arising from a polymerization of a mixture of unsaturated monomers, and each set being distinguishable from another by virtue of a unique fluorescent or non-fluorescent signature. In a preferred embodiment, a unique fluorescent or non-fluorescent signature arises from exposure of microspheres of each set to a unique mixture comprising one or more fluorescent or non-fluorescent dyes. In another preferred embodiment, a unique mixture comprising one or more fluorescent dyes is obtained by varying a concentration of at least one of a mixture comprising one or more fluorescent or non-fluorescent dyes. The one or more fluorescent or non-fluorescent dyes may differ, of course, by their chemical structures.

A core particle comprising a cross-linked or non-cross-linked polymer composition arising from a polymerization of a mixture of unsaturated monomers, including t-butyl-styrene, is provided. Also provided is a microsphere comprising a core particle comprised of a cross-linked or non-cross-linked polymer composition arising from a polymerization of a mixture of unsaturated monomers, including t-butylstyrene, which microsphere has been dyed by contacting the microsphere with a mixture comprising one or more fluorescent or non-fluorescent dyes. Further provided is a population having two or more sets of microspheres, either segregated by set or combined, each microsphere of each set comprising (i) a core particle comprised of first cross-linked or non-cross-linked polymer composition arising from a polymerization of a mixture of unsaturated monomers, including t-butylstyrene, each set being distinguishable from another by virtue of a unique fluorescent or non-fluorescent signature.

Importantly, a microsphere of the instant disclosure may have a density falling in a range of about 0.95 g/cm$^3$ to about 1.05 g/cm$^3$, preferably in a range of about 0.85 g/cm$^3$ to about 0.95/cm$^3$, and more preferably in a range of about 0.90 g/cm$^3$ to about 1.00 g/cm$^3$. A microsphere of the instant disclosure may also have a density falling in a range of about 0.85 g/cm$^3$ to about g/cm$^3$, preferably in a range of about 0.90 g/cm$^3$ to about 0.95 g/cm$^3$, and more preferably in a range of about 0.95 g/cm$^3$ to about 1.00 g/cm$^3$, and even more preferably in a range of about 1.00 g/cm$^3$ to about 1.05 g/cm$^3$, or even as high as about 1.10 g/cm$^3$, or about 1.15 g/cm$^3$, or about 1.20 g/cm$^3$.

In one embodiment, the mixture of unsaturated monomers includes one that is a cross-linker, or includes one that introduces surface functional groups. Moreover, the magnetic particles comprise one or more metal oxides, or comprise ferromagnetic metal oxides, paramagnetic metal oxides, superparamagnetic metal oxides, or combinations thereof. The one or more metal oxides is selected from the group consisting of $Fe_2O_3$, $MnFe_2O_4$, $CoFe_2O_4$, $ZnFe_2O_4$ and $NiFe_2O_4$. Most preferably, the one or more metal oxides comprises $Fe_3O_4$ (magnetite).

A suitable anhydride may be selected from the group consisting of acetic anhydride, 1,2-benzenedicarboxylic anhydride, maleic anhydride, succinic anhydride and combinations thereof, A suitable free radical initiator is selected from the group consisting of azo compounds, organic peroxides and inorganic peroxides. A suitable cross-linker is selected from the group consisting of divinylbenzene, ethylene glycol dimethacrylate, butadiene, trimethylol propane trimethacrylate, N,N'-methylene-bis-acrylamide and combinations thereof. A suitable monomer that introduces a surface functional group is selected from one that provides a carboxyl, amino, sulfhydryl, epoxy, hydroxy, halide and other heteroatom containing functional group.

As described herein, a molecular diagnostic assay is provided, which comprises a microsphere having a core particle comprised of first cross-linked or non-cross-linked polymer composition arising from a polymerization of a mixture of unsaturated monomers, including t-butylstyrene, which microsphere has been dyed by contacting the microsphere with a mixture comprising one or more fluorescent or non-fluorescent dyes, and a plurality of moieties bound to a surface of the microsphere, which moieties are designed to detect an analyte, or interact with a substrate, that might be present in a sample. Preferably, the plurality of moieties is selected from affinity proteins or reagents, antigens, antibodies, oligopeptides, oligonucleotides, DNA, RNA and enzymes. In a preferred embodiment, the first, cross-linked polymer composition arises from a polymerization of a mixture comprising t-butylstyrene, styrene, divinylbenzene and acrylic acid, and the second cross-linked polymer composition arises from a polymerization of a mixture comprising styrene, divinylbenzene and acrylic acid, in an important aspect of the technology disclosed herein, a core particle is provided, which comprises a non-cross-linked polymer composition arising from a polymerization of a mixture of unsaturated monomers, including t-butylstyrene. Also important, is a notion of a microsphere that comprises a core particle comprised of a non-cross-linked polymer composition arising from a polymerization of a mixture of unsaturated monomers, including t-butylstyrene, which microsphere has been dyed by contacting the microsphere with a mixture comprising one or more fluorescent or non-fluorescent dyes.

The following examples are not to be considered limiting embodiments of the technology and are provided herein for example purposes only.

EXAMPLES

Example 1. Preparation of Magnetite Particles without Isolation of Larger Magnetic Particles 0.2 moles of iron(III) chloride hexahydrate and 0.1 mole of iron(II) chloride tetrahydrate were dissolved in 400 mL of deionized water in a three-neck round bottom flask with overhead stirring. This mixture was heated to 90° C., with continued stirring. Next, 520 mL of 6N NaOH were added dropwise over a period of 1 hour. The reaction was allowed to continue for another 24 hours.

Example 2. Monolayer of Magnetite Even Coating Core Particle and Outer Polymer Coating 10.2 g of commercially available polystyrene core microspheres with a functionalized carboxylated surface modification were suspended in a total volume of 100 mL methanol. Next, 12.4 mL of the magnetite solution prepared from Example 1 were washed with deionized water, followed by two washes in 1 M HCL, and finally two washes with methanol, Each wash step was accompanied by vigorous stirring and/or sonication in an attempt to break up any aggregates of magnetite particles, Importantly, no centrifugation at approximately 4000×g to separate the larger magnetic particles from the smaller magnetic particles was carried out. The magnetite was re-suspended in a total volume of 100 mL of methanol. The magnetite and the core microspheres were combined and allowed to mix for 3 hours. This mixture was then washed four times with deionized water, and then re-suspended in a total volume of 375 mL of water and charged to a 500 mL three-neck round bottom flask.

An outer layer of polymer composition was prepared by assembling a mixture of 12.6 g distilled styrene, 0.768 g distilled divinylbenzene, 0.173 g benzoyl peroxide and 1.47 g acrylic acid and charging to the above-referenced 500 mL three-neck round bottom flask containing the magnetite particles with this mixture. The mixture was then heated to 60° C. for 24 hours. The resulting polymer coated microspheres were washed with methanol, tetrahydrofuran, followed by three additional washes with methanol, once with water, and finally re-suspended in deionized water.

Example 3. Preparation of Standard (100% polystyrene) Core Particles 25 mL of a 30% (w/v) solids "seed" polystyrene microsphere, obtained from Bangs Laboratories, Inc, (www.bangslabs.com, cat, no, PS04001, nominal diameter 1 micron), were suspended in a 4000 mL of an aqueous solution that is 0.4% (w/w) dioctyl sulfosuccinate, sodium salt (SDS) and 0.2% (w/w) polyvinylpyrrolidone. Next, 390 g styrene monomer, 20 g divinylbenzene, 45 g acrylic acid and 19 g benzoyl peroxide were added to the preceding surfactant/ stabilizer mixture containing seed microspheres. The resulting mixture was added to a 5 L round bottom flask equipped with an overhead stirrer set to rotate at 300 rpm. This mixture was allowed to stir at room temperature for 24-36 hours.

After stirring for 24-36 hours at room temperature, the mixture was heated to 71° C. for 25 hours.

Example 4. Preparation of Buoyant (50% styrene, 50% 4-t-butylstyrene) Core Particles 25 mL of a 30% (w/v) solids "seed" polystyrene microsphere, obtained from Bangs Laboratories, Inc, (www.bangslabs.com, cat. no. PS04001, nominal diameter 1 micron), were suspended in a 4000 mL of an aqueous solution that is 0.4% (w/w) dioctyl sulfosuccinate, sodium salt (SDS) and 0.2% (w/w) polyvinylpyrrolidone, Next, 194 g styrene monomer, 194 g 4-t-butylstyrene, 20 g divinylbenzene, 45 g acrylic acid and 19 g benzoyl peroxide were added to the preceding surfactant/stabilizer mixture containing seed microspheres. The resulting mixture was added to a 5 L round bottom flask equipped with an overhead stirrer set to rotate at 300 rpm. This mixture was allowed to stir at room temperature for 24-36 hours.

After stirring for 24-36 hours at room temperature, the mixture was heated to 71° C. for 25 hours.

Figure 8A:
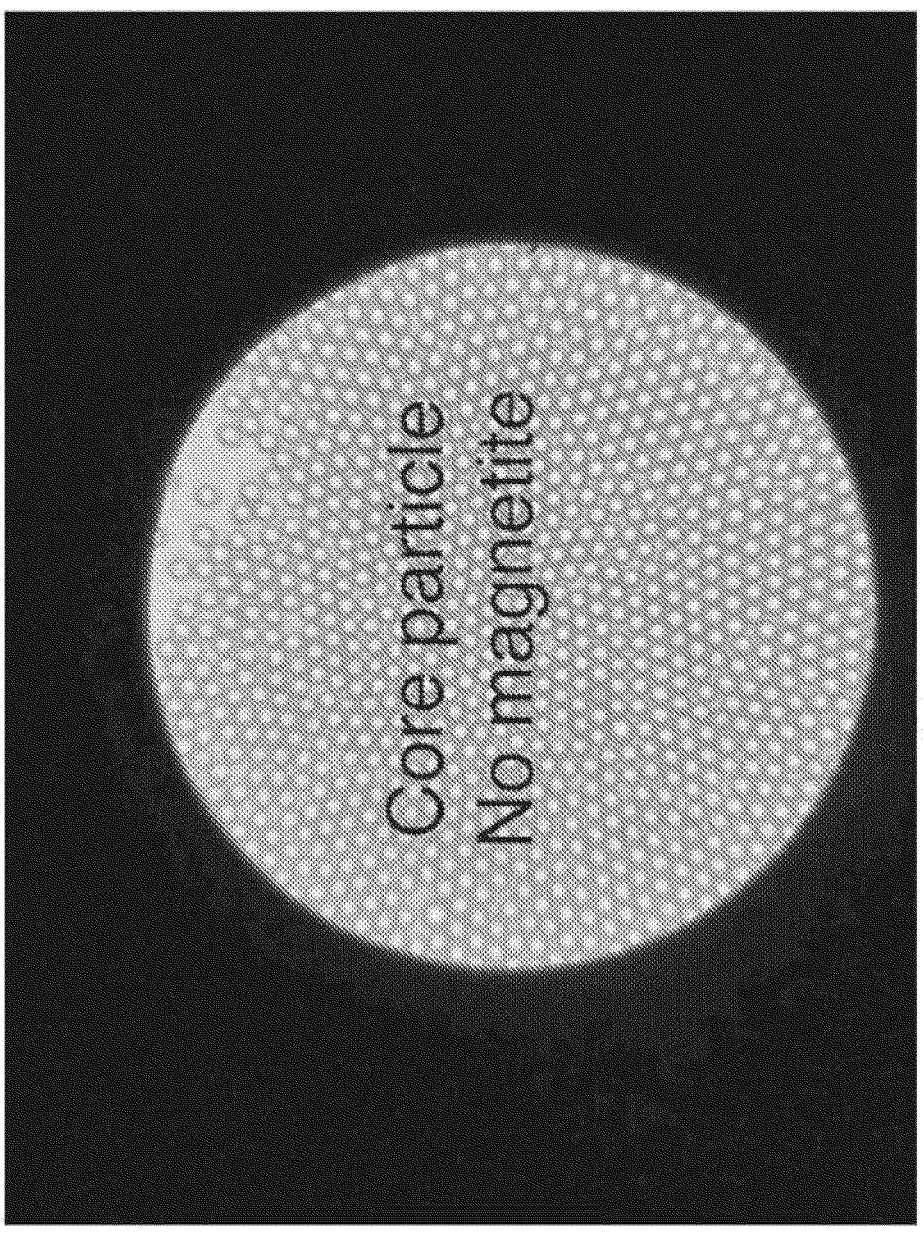

FIG. 8A presents an image from a microscope slide (400×) of 7.2 μm 50% polystyrene, 50% 4-t-butylstyrene low-density (LD) core particles prepared by this method.

Example 5. Preparation of Buoyant (20% styrene, 80% 4-t-butylstyrene) Core Particles 25 mL of a 30% (w/v) solids "seed" polystyrene microsphere, obtained from Bangs Laboratories, Inc, (www.bangslabs.com, cat. no. PS04001, nominal diameter 1 micron), were suspended in a 4000 mL of an aqueous solution that is 0.4% (w/w) dioctyl sulfosuccinate, sodium salt (SDS) and 0.2% (w/w) polyvinylpyrrolidone. Next, 77.6 g styrene monomer, 310.4 g 4-t-butylstyrene, 20.0 g divinylbenzene, 45.0 g acrylic acid and 19.0 g benzoyl peroxide were added to the preceding surfactant/stabilizer mixture containing seed microspheres. The resulting mixture was added to a 5 L round bottom flask equipped with an overhead stirrer set to rotate at 300 rpm. This mixture was allowed to stir at room temperature for 24-36 hours.

After stirring for 24-36 hours at room temperature, the mixture was heated to 71 for 25 hours.

Example 6, Preparation of Buoyant (10% styrene, 90% 4-t-butylstyrene) Core Particles 25 mL of a 30% (w/v) solids "seed" polystyrene microsphere, obtained from Bangs Laboratories, Inc, (www.bangslabs.com, cat, no. PS04001, nominal diameter 1 micron), were suspended in a 4000 mL of an aqueous solution that is 0.4% (w/w) dioctyl sulfosuccinate, sodium salt (SDS) and 0.2% (w/w) polyvinylpyrrolidone. Next, 38.8 g styrene monomer, 349.2 g 4-t-butyl styrene, 20.0 g divinylbenzene, 45.0 g acrylic acid and 19.0 g benzoyl peroxide were added to the preceding surfactant/stabilizer mixture containing seed microspheres. The resulting mixture was added to a 5 L round bottom flask equipped with an overhead stirrer set to rotate at 300 rpm. This mixture was allowed to stir at room temperature for 24-36 hours.

After stirring for 24-36 hours at room temperature, the mixture was heated to 71° C. for 25 hours.

Example 7. Preparation of Magnetic (Magnetite) Particles 27.02 g Fe(III)Cl$_3$·6H$_2$O and 9.94 g Fe(II)Cl$_2$·4H$_2$O were dissolved in 133.3 g water. To this iron salt mixture was added 173.3 g of 6N sodium hydroxide. The resulting basic mixture was heated to 85° C. for 24 hours. See, below, for further washing, ultrasonicating and vigorous mixing steps—but no size selection steps.

Example 8, Generic Procedure for Applying a Monolayer of Magnetic Particles to Core Particles 120 mL of magnetite from Example 7 were washed twice with an equivalent amount of water, followed by two washing using methanol. Each resuspension was vigorously disrupted with ultrasonication and vortex mixing in an effort to break down any aggregates of magnetite. No size separation or selection was carried out during any of these steps.

The processed magnetite was re-suspended in 1000 mL of methanol and added to a 5 L flask equipped with a stirrer.

Figure 2:
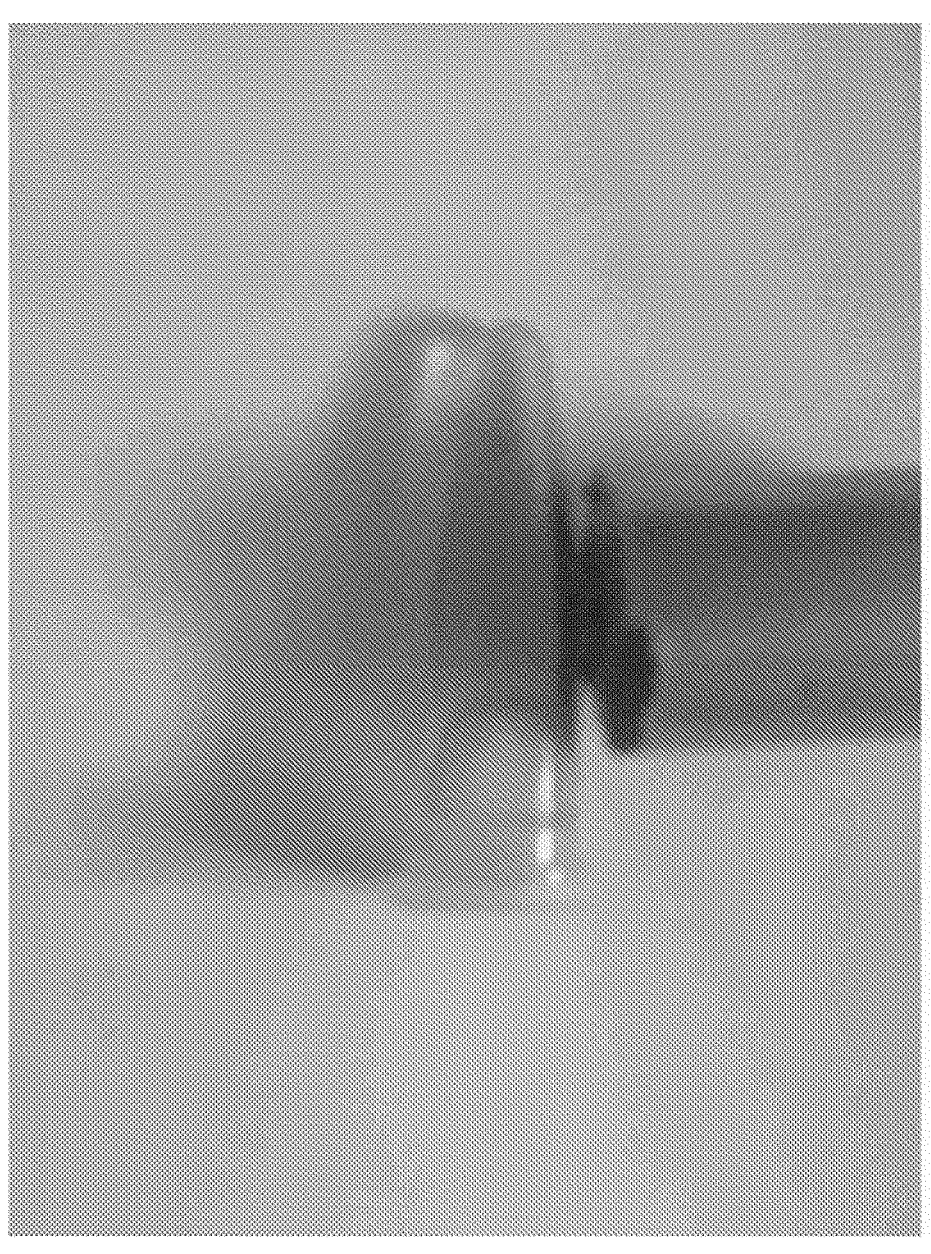
FIG. 2 is an optical image of the next generation microspheres of FIG. 1, but in a presence of an external magnetic field. Notice how the microspheres have pooled to one side of the Eppendorf tube.
Figure 8B:
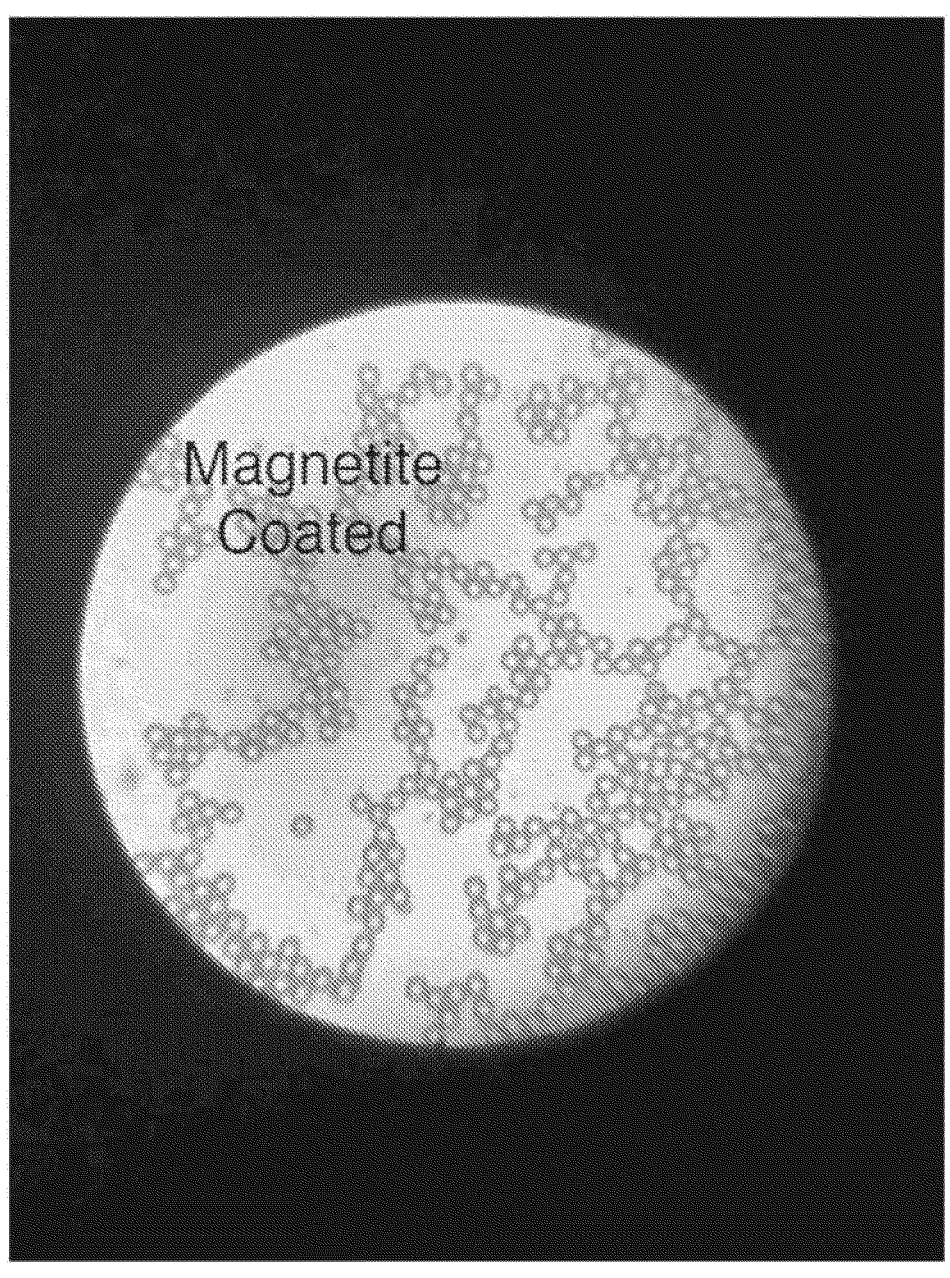

100.0 g core particles from any of the prior Examples, above, were re-suspended in 1000 mL of methanol and added to the aforementioned re-suspended magnetite. After stirring for 24 hours, the resulting magnetic field sensitive microspheres were washed twice with water, followed by two washings with ethyl alcohol, then dried under vacuum. Referring now to the drawings, FIG. 1 is an optical image of an. Eppendorf tube containing next generation microspheres suspended/dispersed in an aqueous solution in an absence of an external magnetic field. FIG. 2 is an optical image of the next generation microspheres of FIG. 1, but in a presence of an external magnetic field. Notice how the microspheres have pooled to one side of the Eppendorf tube. Core particles from Example 6 were treated with magnetic particles according to the disclosed methods. A monolayer of magnetic particles evenly coating a substantial portion of the outer surface of the core particle is evident from scanning electron microscopy (SEM) images shown, with increasing magnification, in FIG. 3, FIG. 4 and FIG. 5. FIG. 8B presents an image from a microscope slide (400×) of 7.2 μm 50% polystyrene, 50% 4-t-butylstyrene LD core particles that have been coated evenly with a monolayer of magnetic particles. The density of the magnetic microspheres depicted in FIG. 8B is estimated to be about 1.04 g/cm$^2$, based on published densities of the pure polymers and estimated magnetite content.

For an interested reader, a review article by Philippova et al. describes other methods for the preparation of magnetic polymer beads: *European Polymer Journal* 47 (2011) 542-559.

Example 9. Generic Procedure for Applying an Outer Layer of Polymer Composition 100.0 g magnetic core particles from Example 8 were re-suspended in 2250.0 g of water in a 5000 mL flask equipped with a stirrer. A mixture of 80.0 g styrene, 5.0 g divinylbenzene, 9.0 g acrylic acid and 1.0 g benzoyl peroxide was added to the aforementioned re-suspended magnetic core particles. The resulting mixture in water was heated to 70° C. for 24 hours. Afterwards, the reaction mixture was allowed to cool, and the product microspheres were washed with methanol and dried under vacuum.

Example 10. A Typical Dyeing Procedure

A single solution containing two different squaric acid dyes was prepared. One dye was a red fluorescent dye, e.g., 1,3-bis[(1,3-dihydro-1,3,3-trim ethyl-2H-indol-2-ylidene) methyl]-2,4-dicyclobutenediylium, bis(inner salt). A second dye was an orange fluorescent dye, e.g., 2-(3,5-dimethylpyrrol-2-yl)-4-(3,5-dimethyl-2H-pyrrol-2-ylidene)-3-hydroxy-2-cyclobuten-1-one. The peak emission of this orange dye is 585 nm, and the peak emission of the red dye is 630 nm. These dyes were chosen because they fall in a center of two of the fluorescence channels of a Becton. Dickinson FACScan™ flow cytometer, which is the measurement device that can be used to determine the precision of any dyeing techniques. The choice of fluorescence channels is, however, relative and immaterial because another flow cytometry apparatus may have different settings. The at least two fluorescent dyes were combined in a solvent mixture comprising at least one organic solvent in which the at least two fluorescent dyes are soluble and at least one alcoholic solvent in which the at least two fluorescent dyes are less soluble, to provide a solution of mixed dyes which is further characterized as having the capacity to swell at least partially but not dissolve a plurality of magnetic microspheres, which were brought into contact with the solution.

A plurality of undyed magnetic microspheres were prepared as described, above, and brought into contact with the dyeing solution for a period of time sufficient to provide uniform staining of substantially all of the members of the plurality of magnetic microspheres with the at least two fluorescent dyes. This process imbues the plurality of magnetic microspheres with a unique fluorescent signature characteristic of a concentration of each fluorescent dye in the dyeing solution. Samples of the dyed magnetic microspheres were measured or read in a FACScan™ flow cytometer or other flow instrument and an X-Y plot was generated to show the relative homogeneity of each sample, X-axis represents brightness or fluorescence intensity of orange dye, and Y-axis represents the same parameters of red dye. Mean intensities and coefficients of variation were also measured. Ideally, the detected intensities spread over a small X-Y area, indicating that the ratio of orange and red dyes varies little from particle-to-particle.

Example 11. Creation of Distinct Sets of Dyed Magnetic Microspheres

To make another population of dyed magnetic beads with a different fluorescent signature, the ratio of red/orange dyes was altered by an adequate increment in a proportion of a dye or both dyes so that resulting dyed population does not overlap in an optical sense with the former population. Thus, this incremental process achieves construction of as many as 500 subsets of optically distinct beads by varying the ratio of just 2 dyes, And with the use of three dyes (say, red, green or orange and blue or violet dyes), this incremental process achieves construction of as many as 1400 subsets of optically distinct beads. This example is not in any way a limiting one because one of ordinary skill may easily generate smaller or higher number of bead subsets by using the instant teaching, One skilled in the art may appreciate that nothing even close to this achievement has ever been enabled in actual practice. Although such an eventuality was theoretically speculated as a possible one, the prior art failed to teach one of ordinary skill how to arrive at that many subsets.

Figure 6:
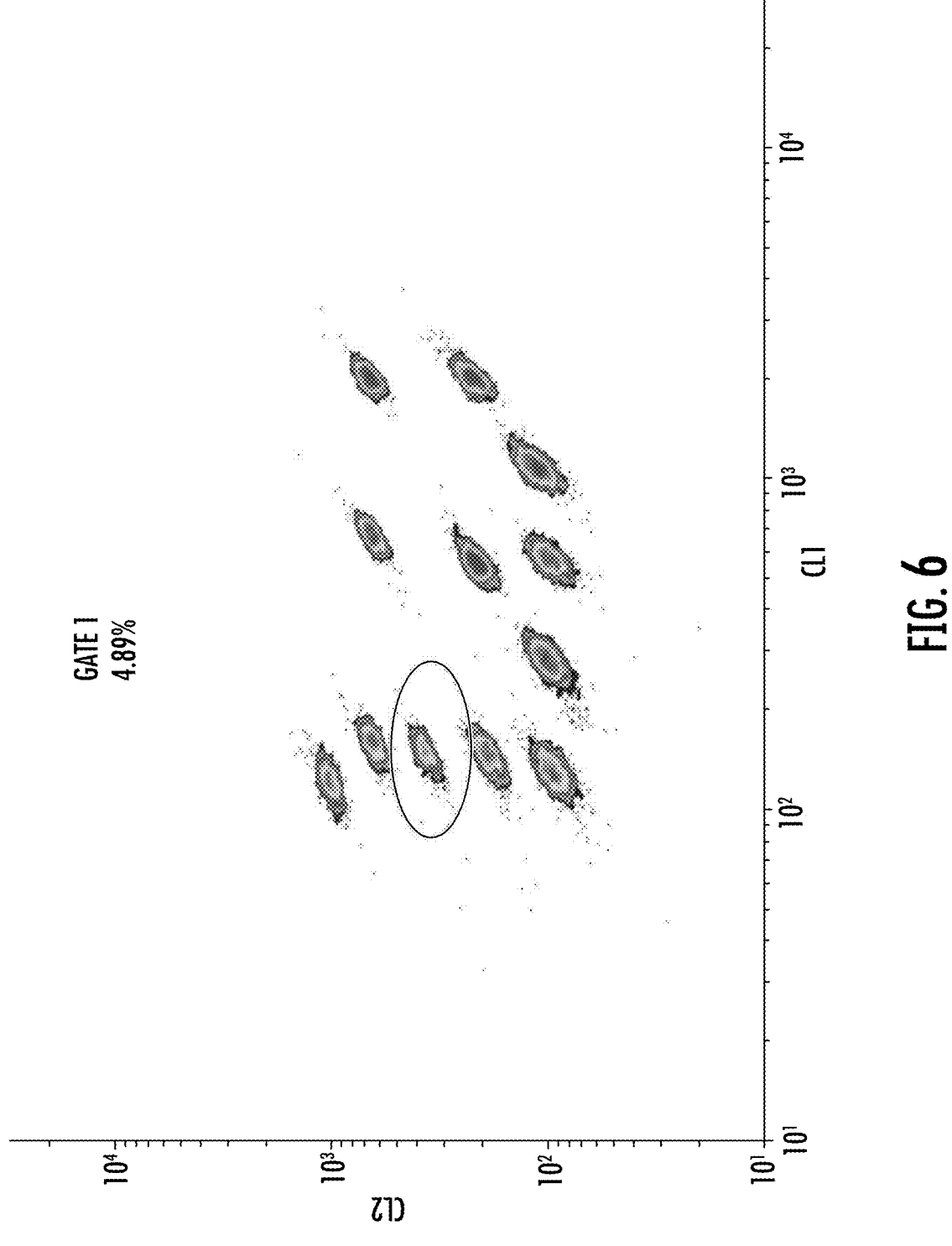
FIG. 6 is an illustration of a 12-plex magnetic microsphere bead set displaying 12 distinct fluorescent signatures.

Illustrative of the products and benefits of this disclosure, a 12-plex magnetic bead set is displayed in FIG. 6. With a use of multiple fluorochromes, and differing concentrations, a three dimensional bead map can be envisioned in which a "planar" 12-plex configuration, such as the one shown in FIG. 6, can be replicated over a third dimension—providing stacked but distinct bead maps. The disclosure provided herein enables the production of as many different bead sets as is required by the current market, including 5-, 10-, 20-, 50-, 100-, 500-, 1000- and 1400-bead sets.

Example 12. Creation of Molecular Diagnostic Assays using Next Generation Microspheres Although multiplexed analysis capability theoretically would provide enormous benefit in the art of flow cytometry, very little progress has been previously achieved due to technical limitations in obtaining sufficient variety of multicolored, non-overlapping subsets of fluorescent magnetic microspheres.

A series of antibodies, antigens, or nucleic acid probes, collectively named hereinafter as analytical reactants, are attached to the beads by any of a number of conventional procedures such as by chemical or physical adsorption as described by Colvin et al., "The Covalent Binding of Enzymes and Immunoglobulins to Hydrophilic Microspheres" in Microspheres: Medical and Biological Applications, 1-13, CRC, Boca Raton, Fla., 1988; Cantarero et al., "The Adsorptive Characteristics of Proteins for Polystyrene and Their Significance in Solid-Phase Immunoassays," Anal Biochem, 105, 375-382(1980); and Illum et al, "Attachment of Monoclonal Antibodies to Microspheres," Methods in Enzymol, 112, 67-84 (1985) 112, 67-84 (1985).

After attachment of a reactant to the beads' surface, aliquots from each subset are mixed to create a pool containing known amounts of beads within each subset. Preferably, the pooled set is prepared with equal volumes of beads from each subset, so that the set contains about the same number of beads from each subset or population. This pool is then be incubated with a fluid sample of interest, such as serum or plasma, to test for the presence of antibodies in the fluid that are reactive with antigens on the beads. Such incubation is generally performed under conditions of temperature, pH, ionic concentrations, and the like that facilitate specific reaction of antibodies in the fluid sample with antigen on the bead surface. After a sufficient period of time, the beads in the mixture are centrifuged, washed and incubated for another period of time with a "secondary" antibody such as, for example, fluorescein labeled goat anti human immunoglobulin. The secondary antibody or label reagent will bind to and fluorescently label antibodies bound to antigen on the beads. After washing (or without washing), the beads are processed by a flow cytometer and the four classification parameters forward light scatter, side light scatter, red fluorescence, and orange (or green) fluorescence (and, optionally, violet fluorescence) are measured and used to identify the subset or population to which each bead belongs. A simultaneous measurement of green fluorescence (measurement parameter) for each bead allows one to determine whether the bead has antibody bound to it. Because the subset to which a bead belongs is correlated with the presence of a particular antigen, e.g., series of grass allergens, various substance abuse drugs, one may readily determine the specificity of the antibody bound to a bead as a function of the subset to which it belongs.

Example 13. Displacement or Competition Assay

Assays for many substances in a clinical laboratory are based on the interference with specific ligand-ligate or antigen-antibody interactions. In these assays, one member of the ligand-ligate pair is labeled with the fluorophore or fluorochrome and one member is immobilized on the beads. Soluble, unlabeled analyte, which may be ligand or ligate, is added to the reaction mixture to competitively inhibit interaction of the labeled component with the immobilized component. It is usually not important which member of the pair is labeled and which is immobilized; however, in certain assays, functional advantages may dictate the orientation of the assay. In an exemplary assay of this type, each bead subset is provided with an antigen. The antigen-coated beads are then reacted with labeled antibody specific for the antigen on the bead surface. Subsequent addition of a test fluid containing soluble analyte (inhibitor) will displace the labeled antibody from the beads in direct proportion to the concentration of the soluble analyte. A standard curve of known analyte concentrations is used to provide accurate quantification of analyte in the test sample.

Example 14. Nucleic Acid Analysis

The power and sensitivity of PCR found its application to a wide variety of analytical problems in which detection of DNA or RNA oligonucleotide sequences is required, One major difficulty with the PCR technique is the cumbersome nature of the methods of measuring end-product, amplified DNA. A flow cytometric bead-based hybridization assay permits the extremely rapid and accurate detection of genetic sequences of interest. In a preferred embodiment of this technology, a bead to which a nucleic acid segment of interest has been coupled is provided. A PCR product of interest (or any other DNA or cDNA segment) is detected by virtue of its ability to competitively inhibit hybridization between the nucleic acid segment on the bead and a complementary fluorescent DNA probe. The method is sensitive and precise and allows the detection of single point mutations in the PCR product or DNA of interest. The multiplexed DNA analysis method can be applied to detect any PCR product or other DNA of interest for specific polymorphisms or mutations and one skilled in the art will recognize that numerous applications can be imagined such as presence of histocompatibility alleles associated with susceptibility to diseases, mutations associated with genetic diseases, autoimmune diseases, or mutations of oncogenes associated with neoplasia or risk of neoplasia. In a same way nucleic acid segments from pathogenic organisms such as bacterial, viral, fungal, mycoplasmal, rickettsial, chlamydial, or protozoan pathogens can be detected simultaneously.

Example 15. Enzyme Assays

The technology is also useful for measurement of enzymes, enzyme inhibitors and other analytes. For example, bead subsets are generated with selected fluorescent substrates which are enzymatically cleaved from the bead, resulting in a loss of fluorescence. Enzymes that can be detected and measured using the technology include but are not restricted to, proteases, glycosidases, nucleotidases, and oxidoreductases. Any enzyme that results in selected bond cleavage can be measured. Alternatively, the action of the enzyme on the bead-bound substrate results in the formation or identification of a ligate for a fluorescent ligand present in the reaction mixture. The bead bearing the modified substrate then becomes fluorescent by virtue of binding of the fluorescent ligand to the newly formed ligate. Because each type of bead bearing the unique substrate can be distinguished, a mixture of bead subsets can be used to measure several enzyme activities simultaneously in the same reaction mixture.

Fluids or samples with analytes that can be analyzed using these techniques include plasma, serum, tears, mucus, saliva, urine, pleural fluid, spinal fluid and gastric fluid, sweat, semen, vaginal secretions, fluid from ulcers and other surface eruptions, blisters, and abscesses, and extracts of tissues including biopsies of normal, malignant, and suspect tissues.

The above examples can be used to perform most common immunodiagnostic and nucleic acid assays. Other applications such as high throughput screening of combinatorial chemistry libraries for discovering new drugs, environmental screening of pollutants, drug testing, food safety-related investigations, testing of multiple analytes for agricultural needs, etc, can be imagined.

Example 16. Scanning Electron Microscopy

A surface texture of core particles from Example 6 (10% polystyrene, 90% 4-t-butylstyrene) evenly coated with a monolayer of magnetic particles (5 wt %) was visualized by scanning electron microscopy (SEM). (See, FIG. 3, FIG. 4 and FIG. 5.) The magnetite coated microspheres are approximately 6 microns in diameter. A low-voltage analysis was used to show surface features. Nanoparticles of magnetite are readily apparent across the surface of the core particles, and the coverage is generally uniform judged by visual inspection (and, in any case, much greater than 50% of the surface area of the core particles). Some recessed areas of the core particles (occasional defects on the surface of some of the core particles) exhibit fewer magnetic particles, presumably because the magnetite coating process did not allow magnetite to reach such inner, recessed areas.

Sample material was dry deposited on a carbon adhesive tab mounted on an aluminum SEM stub. A coating of iridium, approximately 2 nm thick, was applied via sputter deposition Analysis was performed using a Hitachi 5-4800 field-emission SEM operated at 2 kV accelerating voltage. Magnetite particles form a monolayer on the surface of the core particles, exhibiting a range of sizes, from less than 10 nm to greater than 100 nm.

Example 17. Magnetic Microsphere Settling Test

Magnetic microspheres were prepared using the above-described procedures starting with standard density 100% polystyrene core particles (SD) on the one hand and buoyant or low density 50% polystyrene. 50% 44-butylstyrene core particles (LD) on the other hand. This experiment was meant to demonstrate an undesirable property of SD microspheres: a settling behavior that is undesirable—promoting aggregation of microspheres and leading to lower particle counts over time, such as the time it takes between sample preparation and reading the sample in a flow instrument or even the time it hakes between reading a first well to reading a last well of a microtiter plate. As shown by the outcome of this experiment. LD microspheres exhibit this undesirable behavior to a much lower degree, it at all.

Two test microtiter plates (96 wells each) were prepared, one using SD microspheres and the other using LD microspheres. Each well contained 70 µL of sample fluid (saline buffer) with a particle concentration of 150 particles per Immediately after all the welts of a plate were filled, the plate was loaded into a flow instrument, and the wells were read one well at a time across each row of the plate. Prior to sample aspiration, the flow instrument agitates a sample by drawing and dispensing 25 µL of fluid from the well. After agitation, 25 µL of sample fluid were aspirated and read. Table A (SD) and Table B (ED) present the total particle count observed from each well. Again, well A1 was read first, followed by well A2 and so on until well H12 was read.

TABLE A

| | | | | | | SD Microspheres | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 3000 | 2896 | 3016 | 3064 | 3152 | 3000 | 3240 | 3136 | 3216 | 3008 | 3096 | 2768 |
| B | 3184 | 3016 | 3112 | 3072 | 3176 | 2936 | 3088 | 2776 | 2840 | 2816 | 2800 | 2464 |
| C | 3096 | 2624 | 3160 | 2856 | 2848 | 2568 | 2656 | 2544 | 2728 | 2568 | 2400 | 2224 |
| D | 3096 | 2608 | 2704 | 2280 | 2576 | 2432 | 2416 | 2392 | 2552 | 2504 | 2496 | 2112 |
| E | 2760 | 2328 | 2480 | 2328 | 2472 | 2344 | 2624 | 2488 | 2584 | 2488 | 2520 | 1976 |
| F | 3056 | 2376 | 2280 | 2416 | 2464 | 2472 | 2616 | 2544 | 2584 | 2256 | 2384 | 2040 |
| G | 3016 | 2920 | 2272 | 2264 | 2384 | 2264 | 2640 | 2520 | 2640 | 2280 | 2280 | 1816 |
| H | 2232 | 1864 | 2328 | 2432 | 2456 | 2664 | 2456 | 2384 | 2600 | 2560 | 2680 | 1760 |

TABLE B

| | | | | | | LD Microspheres | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 3144 | 3184 | 3144 | 3280 | 3232 | 3184 | 3160 | 3160 | 3208 | 3176 | 3200 | 3088 |
| B | 3264 | 6240 | 3208 | 3272 | 3104 | 3248 | 3168 | 3224 | 3240 | 3464 | 3104 | 3104 |
| C | 3192 | 3192 | 3264 | 3248 | 3184 | 3112 | 3240 | 3168 | 3176 | 3088 | 3184 | 3024 |
| D | 3096 | 3088 | 3136 | 3232 | 3120 | 3144 | 3192 | 3200 | 3112 | 3112 | 3000 | 2992 |
| E | 3112 | 3160 | 3184 | 3024 | 3392 | 2824 | 3032 | 3040 | 3080 | 2856 | 3040 | 2992 |
| F | 3112 | 3160 | 3184 | 3024 | 3392 | 2824 | 3032 | 3040 | 3080 | 2856 | 3040 | 2888 |
| G | 3144 | 2888 | 2936 | 3160 | 3320 | 2840 | 2864 | 3024 | 3152 | 2984 | 2880 | 2840 |
| H | 2672 | 2648 | 2848 | 2640 | 2888 | 2840 | 2912 | 3096 | 3128 | 3160 | 2832 | 2680 |

Figure 7A:
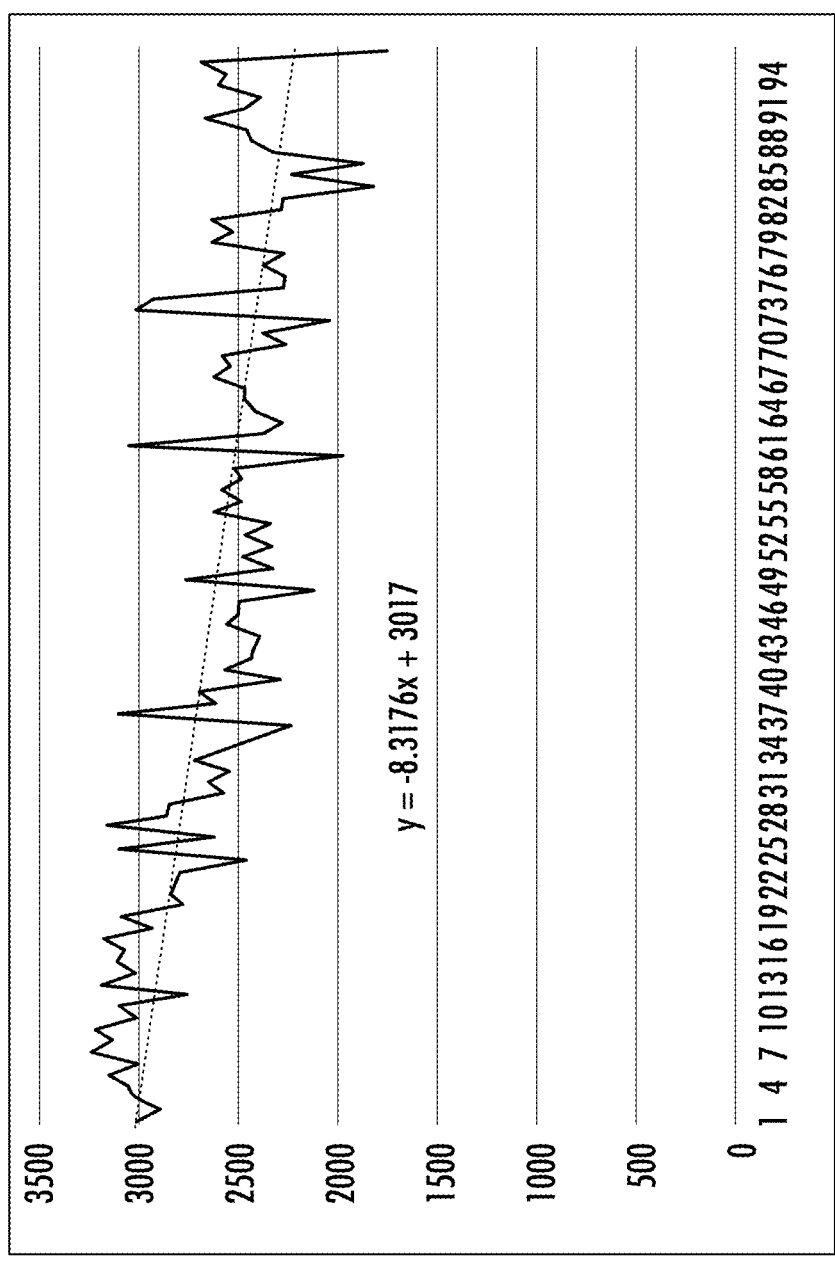
FIG. 7A. A plot of data from particle counts observed from 96 consecutive measurements using conventional SD microspheres.
Figure 7B:
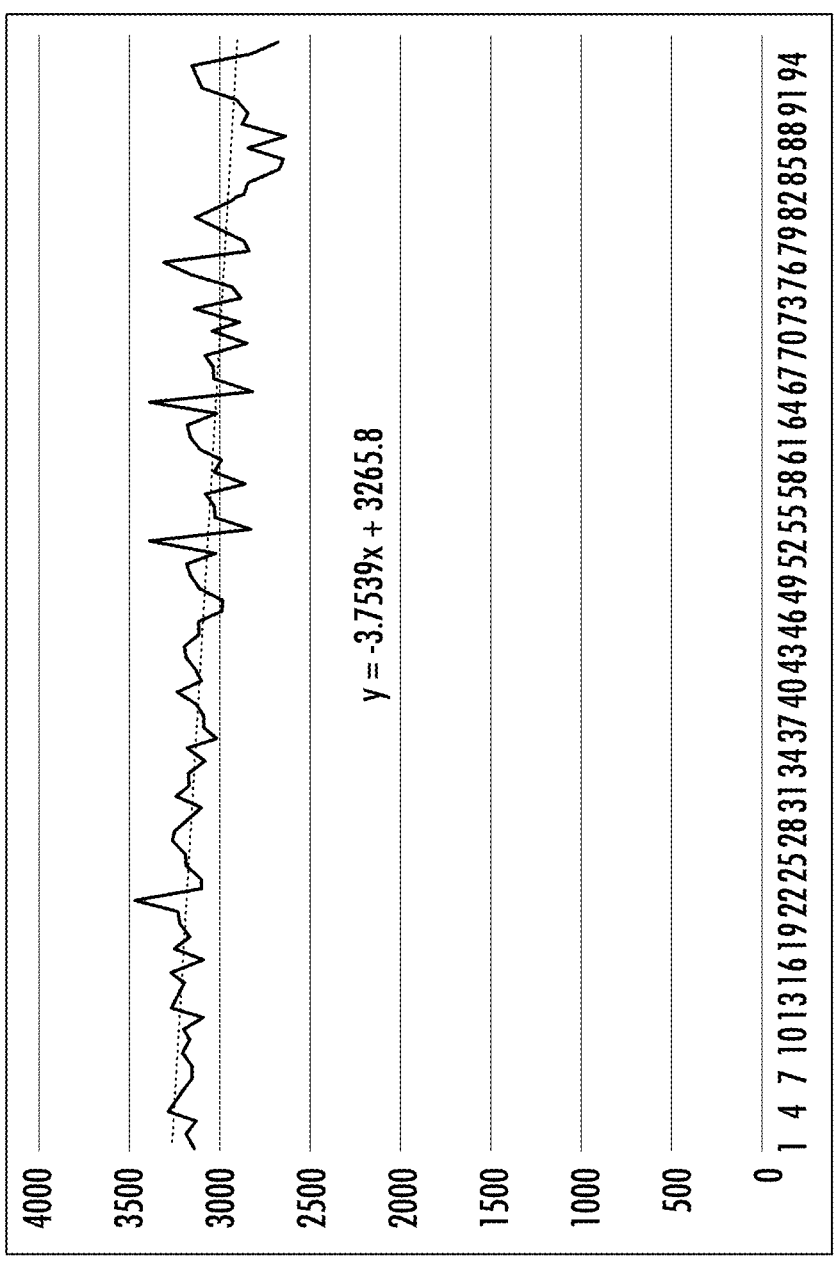
FIG. 7B, A plot of data from particle counts observed from 96 consecutive measurements using buoyant or low density LD microspheres, FIG. 8A. Image from a microscope slide (400×) of 7.2 μm 50% polystyrene, 50% 4-t-butylstyrene LD core particles, FIG. 8B. Image from a microscope slide (400×) of 7.2 μm 50% polystyrene, 50% 4-t-butylstyrene LD core particles that have been coated evenly with a monolayer of magnetic particles.

The data from each row of a 96-well plate were rearranged to reflect consecutive readings of all 96 wells, Such a format allowed total panicle count to be plotted against limo, FIG. 7 depicts the resulting graph using data from SD microspheres, and FIG. 7B depicts the resulting graph using data from LD microspheres. The graphs show that the LD microspheres settle at less than half the rate of conventional SD microspheres. The slope of the regression line shows that particle counts drop about 4.15% per minute with conventional SD microspheres compared with a drop of less than 1.87% per minute with buoyant car low density LD microspheres (i.e., the slope of the LDs is less than half that of the SDs). It should be noted that the results reveal evidence of dinning or aggregation of conventional SD microspheres, leading to significant well-to-well variations. In particle counts compare the severe jagged spikes from the SD microspheres data set compared to the relative quiescence from the LD microspheres data set).

It is to be understood that, while the foregoing technology has been described in detail by way of illustration and example of preferred embodiments, numerous modifications, substitutions, and alterations are possible without departing from the spirit and scope of the technology as described in the following claims.

Further modifications and alternative embodiments of various aspects of the technology may be apparent to those skilled in the art in view of this description. For example, microspheres and populations of microspheres that are configured to exhibit fluorescent and magnetic properties are provided. Accordingly, this description is to be construed as illustrative only and is for the purpose of teaching those skilled in the art the general manner of carrying out the ID technology. It is to be understood that the forms of the technology shown and described herein are to be taken as the presently preferred embodiments. Elements and materials may be substituted for those illustrated and described herein, parts and processes may be reversed, and certain features of the technology may be utilized independently, all as would be apparent to one skilled in the art after having the benefit of this description of the technology. Changes may be made in the elements described herein without departing from the spirit and scope of the technology as described in the following claims.

Figure 3:
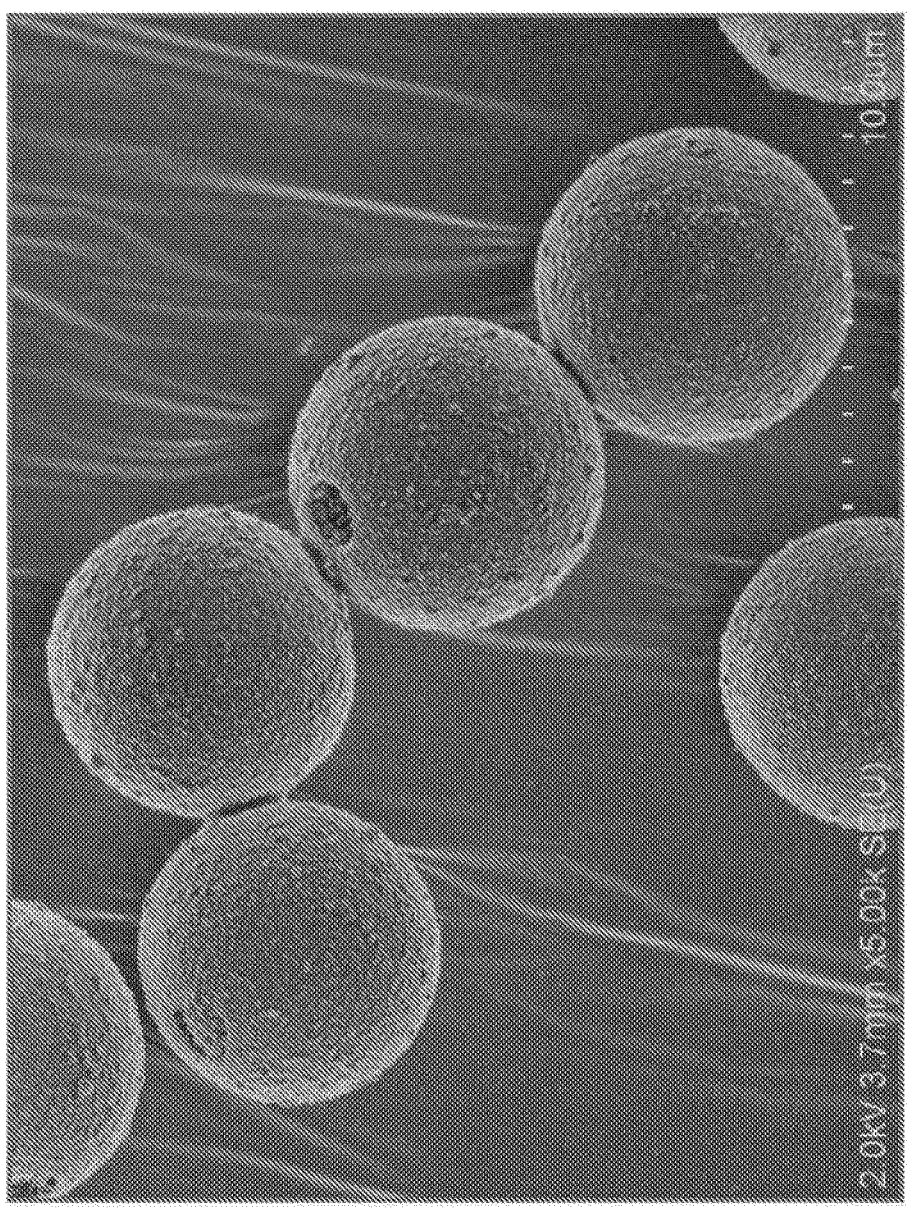
FIG. 3 is an SEM image of core particles coated with a monolayer of magnetic particles at a magnification of 5,000×.
Figure 4:
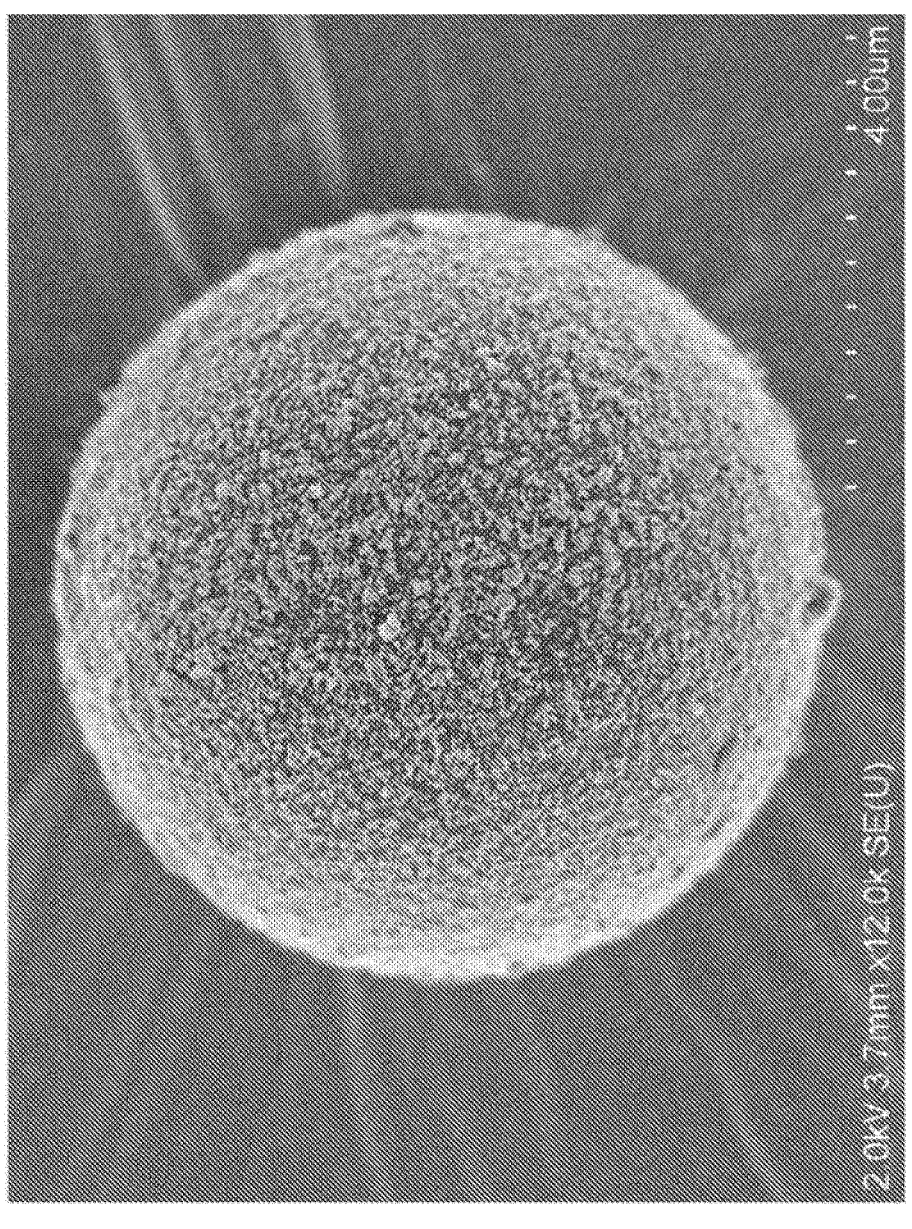
FIG. 4 is an SEM image of core particles coated with a monolayer of magnetic particles at a magnification of 12,000×.
Figure 5:
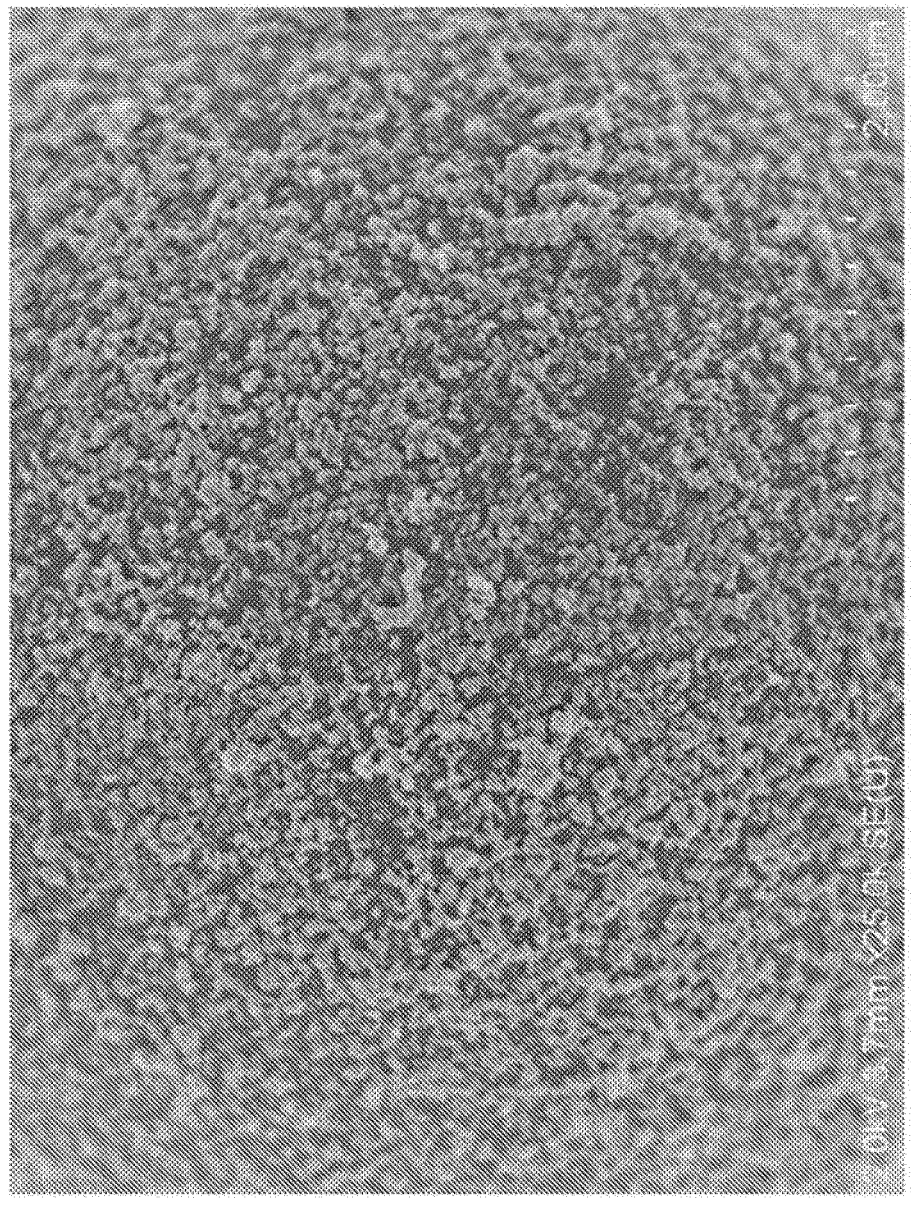
FIG. 5 is an SEM image of core particles coated with a monolayer of magnetic particles at a magnification of 25,000×.

In some embodiments, FIG. 1 is or includes an optical image of an Eppendorf tube containing next generation microspheres suspended/dispersed in an aqueous solution in an absence of an external magnetic field. In some embodiments, is or includes an optical image of the next generation microspheres of FIG. 1, but in a presence of an external magnetic field, Notice how the microspheres have pooled to one side of the Eppendorf tube. In some embodiments, FIG. 3 shows core particles coated with a monolayer of magnetic particles at a magnification of 5000×. In some embodiments, FIG. 4 shows core particles coated with a monolayer of magnetic particles at a magnification of 12,000×. In some embodiments, FIG. 5 shows core particles coated with a monolayer of magnetic particles at a magnification of 25,000×, In some embodiments, FIG. 6 shows A 12-plex magnetic microsphere bead set displaying 12 distinct fluorescent signatures. In some embodiments, FIG. 7A shows a plot of data from particle counts observed from 96 consecutive measurements using conventional. SD microspheres. In some embodiments, FIG. 7B a plot of data from particle counts observed from 96 consecutive measurements using buoyant or low density LD microspheres. In some embodiments, FIG. 8A shows an image from a microscope slide (400×) of 7.2 μm 50% polystyrene, 50% 4-t-butylstyrene LD core particles. In some embodiments, FIG. 8B shows an image from a microscope slide (400×) of 72 μm 50% polystyrene, 50% 4-t-butylstyrene LD core particles that have been coated evenly with a monolayer of magnetic particles.

What is claimed is:

1. A microsphere comprising (i) a core particle comprised of a first cross-linked or non-cross-linked polymer composition arising from a polymerization of a mixture of unsaturated monomers, including t-butylstyrene, said core particle having an outer surface, (ii) a monolayer of magnetic particles evenly coating a substantial portion of said outer surface of said core particle, and (iii) an outer layer of a second cross-linked or non-cross-linked polymer composition arising from a polymerization of a mixture of unsaturated monomers, and which microsphere has a density falling in a range of about 0.95 to about 1.10 g/mL.

2. The microsphere of claim 1 in which said monolayer of magnetic particles evenly coats at least 60% of the outer surface of said core particle.

3. The microsphere of claim 1 in which said monolayer of magnetic particles evenly coats at least 90% of the outer surface of said core particle.

4. The microsphere of claim 1 in which said monolayer of magnetic particles evenly coats between 60% and 90% of the outer surface of said core particle.

5. The microsphere of claim 1 in which said microsphere has a density falling in a range of about 1.0 to about 1.05 g/mL.

6. The microsphere of claim 1 in which said mixture of unsaturated monomers includes one that is a cross-linker.

7. The microsphere of claim 1 in which said mixture of unsaturated monomers includes one that introduces surface functional groups.

8. The microsphere of claim 1 in which said magnetic particles comprise one or more metal oxides.

9. The microsphere of claim 1 in which said magnetic particles comprise ferromagnetic metal oxides, paramagnetic metal oxides, superparamagnetic metal oxides, or combinations thereof.

10. A microsphere comprising (i) a core particle comprised of a first cross-linked or non-cross-linked polymer composition arising from a polymerization of a mixture of unsaturated monomers, including t-butylstyrene, said core particle having an outer surface, (ii) a monolayer of magnetic particles evenly coating a substantial portion of said outer surface of said core particle, and (iii) an outer layer of a second cross-linked or non-cross-linked polymer composition arising from a polymerization of a mixture of unsaturated monomers, and which microsphere has a density falling in a range of about 0.95 to about 1.10 g/mL and has been dyed by contacting said microsphere with a mixture comprising one or more fluorescent or non-fluorescent dyes.

11. The microsphere of claim 10 in which said monolayer of magnetic particles evenly coats at least 60% of the outer surface of said core particle.

12. The microsphere of claim 10 in which said monolayer of magnetic particles evenly coats at least 90% of the outer surface of said core particle.

13. The microsphere of claim 10 in which said monolayer of magnetic particles evenly coats between 60% and 90% of the outer surface of said core particle.

14. The microsphere of claim 10 which possess a unique fluorescent or non-fluorescent signature.

15. The microsphere of claim 14 in which said unique fluorescent or non-fluorescent signature arises from exposure to a unique mixture comprising one or more fluorescent or non-fluorescent dyes.

16. The microsphere of claim 15 in which the unique mixture comprising one or more fluorescent or non-fluorescent dyes is obtained by varying a concentration of at least one of a mixture comprising one or more fluorescent or non-fluorescent dyes.

17. A population having two or more sets of microspheres, either segregated by set or combined, each microsphere of each set comprising (i) a core particle comprised of a first cross-linked or non-cross-linked polymer composition arising from a polymerization of a mixture of unsaturated monomers, including t-butylstyrene, said core particle having an outer surface, (ii) a monolayer of magnetic particles evenly coating a substantial portion of said outer surface of said core particle, and (iii) an outer layer of a second cross-linked or non-cross-linked polymer composition arising from a polymerization of a mixture of unsaturated monomers, and in which each microsphere has a density falling in a range of about 0.95 to about 1.10 g/mL, and each set being distinguishable from another by virtue of a unique fluorescent or non-fluorescent signature.

18. The population of claim 17 in which the unique fluorescent or non-fluorescent signature arises from exposure of microspheres of each set to a unique mixture comprising one or more fluorescent or non-fluorescent dyes.

19. The population of claim 18 in which the unique mixture comprising one or more fluorescent or non-fluorescent dyes is obtained by varying a concentration of at least one of a mixture comprising one or more fluorescent or non-fluorescent dyes.

20. The population of claim 18 in which said one or more fluorescent or non-fluorescent dyes differ by their chemical structures.

* * * * *